(12) United States Patent
Guariglia et al.

(10) Patent No.: US 8,901,037 B2
(45) Date of Patent: Dec. 2, 2014

(54) COMPOSITION HAVING A GERMINATION-PREVENTING ACTIVITY, PROCESSES FOR OBTAINING SAID COMPOSITIONS AND USE THEREOF

(75) Inventors: Francesco Guariglia, Pagani (IT); Pio Iannelli, Salerno (IT); Paola Scarfato, Baronissi (IT)

(73) Assignee: Isagro S.p.A., Milan (IT)

( * ) Notice: Subject to any disclaimer, the term of this patent is extended or adjusted under 35 U.S.C. 154(b) by 439 days.

(21) Appl. No.: 12/309,009

(22) PCT Filed: Jun. 26, 2007

(86) PCT No.: PCT/EP2007/005699
§ 371 (c)(1),
(2), (4) Date: Dec. 31, 2008

(87) PCT Pub. No.: WO2008/003423
PCT Pub. Date: Jan. 10, 2008

(65) Prior Publication Data
US 2009/0203525 A1 Aug. 13, 2009

(30) Foreign Application Priority Data

Jul. 4, 2006 (IT) .............................. RM2006A0346

(51) Int. Cl.
*A01N 47/40* (2006.01)
*A01N 29/02* (2006.01)
*A01N 47/46* (2006.01)
*A01N 47/08* (2006.01)

(52) U.S. Cl.
CPC .............. *A01N 29/02* (2013.01); *A01N 47/46* (2013.01); *A01N 47/08* (2013.01)
USPC ......................................................... 504/141

(58) Field of Classification Search
None
See application file for complete search history.

(56) References Cited

U.S. PATENT DOCUMENTS

| | | | | |
|---|---|---|---|---|
| 5,756,542 | A * | 5/1998 | Kojima et al. | 514/514 |
| 6,051,233 | A * | 4/2000 | Champon | 424/736 |
| 6,923,937 | B2 * | 8/2005 | Storkan et al. | 422/32 |
| 2007/0042011 | A1 * | 2/2007 | Wakaki et al. | 424/405 |

FOREIGN PATENT DOCUMENTS

| | | | |
|---|---|---|---|
| JP | 2003144904 A * | 5/2003 | ............... B01J 13/16 |
| WO | WO03/065808 A | 8/2003 | |
| WO | WO2004/067552 A | 8/2004 | |
| WO | WO 2005044003 A1 * | 5/2005 | |
| WO | WO2006116817 A1 * | 11/2006 | |

OTHER PUBLICATIONS

Norsworthy and Meehan, Herbicidal activity of eight isothiocyanates on Texas *Panicum* (*Panicum texanum*), large crabgrass (*Digitaria sanguinalis*), and sicklepod (*Senna obtusifolia*), Weed Science 53: 515-520 (2005).*
Ajwa et al., Phytopathol Mediterr 42: 220-244 (2003).*
PCT Search Report dated May 26, 2008.
Valkova, O. ,Chemical Abstracts 1984:402225 (XP-002477951), 1984.
Norsworthy, Jason K.,Chemical Abstracts 2005:1326517 (XP-002477952), 2005.
Norsworthy, Jason K. ,Chemical Abstracts 2005:714945 (XP-002477953), 2005.
Vaughn, Steven F. , Chemical Abstracts 1997-609106 (XP-002477954), 1997.
Matarai, Masafumi , Chemical Abstracts 1998:298991 (XP-002477956), 1997.
Derwent Publications 2004-136270, (XP-002477957), 2003.
Derwent Publications 1997-113412 (XP-002477958, 1995.
Derwent Publications 1997-128641 (XP-002162143), 1995.
Derwent Publications 1995-151783 (XP-002477959), 1995.
Derwent Publications, 2001-135479 (XP002477960), 2000.

* cited by examiner

*Primary Examiner* — Sue Liu
*Assistant Examiner* — Thor Nielsen
(74) *Attorney, Agent, or Firm* — Hedman & Costigan, P.C.; James V. Costigan; Kathleen A. Costigan (57) ABSTRACT

A composition having a germination-preventing activity, comprising, as active principle, allyl isothiocyanate alone or in combination with other substances having a synergic action, in the form of emulsifiable formulates or as a microencapsulate in which allyl isothiocyanate is englobed in a polymeric-based system for the controlled release of the active principle. The microcapsule membrane represents a weight percentage of 5-25%, the surfactant 2-10% and allyl isothiocyanate a weight percentage not lower than 70%.

10 Claims, 5 Drawing Sheets

COMPOSITION HAVING A GERMINATION-PREVENTING ACTIVITY, PROCESSES FOR OBTAINING SAID COMPOSITIONS AND USE THEREOF

FIELD OF THE INVENTION

The present invention relates to compositions having a germination-preventing activity, the processes for obtaining said compositions and relative uses, in particular in the treatment of agricultural soil.

STATE OF THE ART

The necessity is felt in agriculture for having weedless cultivated fields. This necessity is satisfied by resorting to the use of specific products to be adopted in agricultural soil.

Within the large classification of phyto-drugs (or pesticides) which can be used in agriculture (for example antibacterial or bacteriostatic agents, anticryptogamics, insecticides, phytohormones, etc.), herbicides are active against weeds by operating on the plants or already-formed seedlings, or impeding the germination of the weeds. These products are called germination inhibitors or germination-preventing products.

In the present description the term "germination-preventing" will be adopted.

The present invention relates to the group of germination-preventing products.

According to the present description, the terms listed have the following meaning.

Biocide: a biocide is an active principle or compound containing one or more active principles, destined for destroying, eliminating, making innocuous, preventing the action or exerting other control effect on any harmful organism with chemical or biological means.

Nematocide: an active principle or formulate containing several active principles suitable for destroying or exerting other control effect specifically on nematodes.

Mustard oil (s): the term mustard oil (s) is used for indicating two different types of oil obtained from mustard seeds:
  a vegetable oil obtained by squeezing the seeds
  an essential oil obtained by grinding the seeds, soaking them in water and extracting the volatile oil by distillation.

Deficiency time: the time between the soil treatment to when it becomes possible to sow without damaging the crops.

The treatment adopted in agriculture on soils with germination-preventing formulates can be carried out in two possible ways:
  before sowing (pre-emergence) subsequently leaving a certain deficiency time (typically 1-2 weeks) for the sowing. In this case, products are used having as short a deficiency time as possible for productivity reasons;
  after sowing (post-emergence) on crops already developing, in this case highly selective products are used, which exert their germination-preventing activity against weeds only, with no damage for the crops; in the contrary case, the herbicide effect has a negative influence on the sown product.

Natural compounds called "mustard oil(s)", which are mainly adopted as biocides and insecticides, are products which can be used as herbicides. Allyl isothiocyanate belongs to this group of products, also wildly used as a biocide, insecticide and nematocide.

Allyl isothiocyanate (also called ITA, CAS number 57-06-7) is a volatile product, very pungent and irritating for human beings and animals, with a bitter smell, extremely reactive, almost insoluble in water.

Compositions containing ITA to be used as insecticides, are known. Patent WO 03/033008 claims the fumigant and insecticide action, in addition to the repellent action, of chemical formulations based on the blend of "heat components" extracted from plants, such as the oily extract of black and white pepper, ginger, etc. and an active component, mustard oil. This formulation is by nature considered to be safer with respect to the environment than other formulates used for the treatment of soil. The use of ITA as a natural component of mustard oil for food is mentioned among the active principles, inserted in a preferred formulate, with a typical concentration of about 4% by weight. A blend of surfactants and natural oils is included in the formulate in order to promote the dispersion of the formulate in water and therefore facilitating its application. The patent claims the use of said formulates in the treatment of soil, environments and food products. As far as the treatment of soil is concerned, the patent does not claim any germination-preventing activity of the formulate. Furthermore, a preferred application is discussed in the description of the application procedures, with the dilution of the formulate in water, obtaining a 5-10% solution by weight of the formulate itself. This solution is administered in a quantity of 3.33% by volume with respect to the total volume of the soil. The diluted solution is injected to a depth of about 30-60 cm, equal to 300-600 $dm^3$ of soil per square meter of soil treated; consequently, in the preferred embodiment, 10-20 liters of diluted solution are required for one square meter of soil. This corresponds approximately, for a 10% diluted solution, to about 1000-2000 g of the concentrated formulate for each square meter of treated soil, corresponding to 40-80 g of ITA.

This means the addition of high quantities of co-formulates in the soil, such as surfactants, soybean oil, benzaldehyde, and "lemon compound". The germination-preventing formulate claimed in the present patent envisages much higher ITA concentrations in the formulate, thus minimizing a useless addition of inert components to the soil. Furthermore, in preferred procedures of soil treatment, according to the present invention, the amounts of ITA used are normally lower than 5 g per square meter.

Controlled release formulations are also known for antibacterial, insecticide, antiseptic applications, for example, containing ITA. In U.S. Pat. No. 5,928,661, the preparation is described of formulates capable of controlling the release rate of volatile substances. In particular, the patent describes the preparation of formulates containing rosin (for example the colophony) as absorbing material and ITA as volatile active principle, contained in quantities not higher than 50% by weight with respect to the rosin, and 40% by weight with respect to the whole formulate, including the various co-formulates. Some substances having a plasticizing action are used as co-formulates, such as fatty acids, esters of fatty acids and waxes. The formulate is a solid homogeneous mixture and can be transformed into fibres, bars, films or powders. The aim is to release, at a controlled rate, the volatile active principles englobed in the rosin matrix. The action claimed is the emission of volatile substances having an aroma, insecticidal, fungicidal and preserving action. The formulates according to the present invention, on the contrary, contain ITA in liquid state and the action claimed is controlled release into the soil, with specific germination-preventing action. Furthermore, unlike what is described in U.S. Pat. No. 5,928, 661, in the present patent, ITA can be contained in amounts higher than 50% and can be released into the soil at a high concentration, thus ensuring a high activity to the advantage of the germination-preventing action.

Water emulsions containing chloropicrin and a component similar to ITA, methyl isothiocyanate (patent application WO 2004067552), are also known. In the above-mentioned patent application, the chloropicrin emulsion is administered using the same ducts adopted for watering the crops. In order to facilitate the distribution and keep undesired corrosion effects of the irrigation ducts on the part of fumigants under control, the formulate mentioned in the patent contains one or more surfactants in quantities ranging from 1 to 50% by weight. The formulation has a biocide action in the soil treatment and can contain fumigants belonging to the group of methyl bromide, chloropicrin, 1,3-dichloropropene(telone), propargyl bromide, dimethyldisulphide, methyl isothiocyanate and mixtures thereof.

The formulates described do not contain allyl isothiocyanate and the patent does not claim the germination-preventing action of the compounds. In particular, methyl isothiocyanate is a very volatile and highly toxic gas, it is normally produced in the soil by the transformation of one of its solid precursors, Metam sodium, commercialized under several trade-marks (for ex. Vapam®).

According to this patent, allyl isothiocyanate is a high-boiling substance (the boiling point of allyl isothiocyanate is 151° C. whereas that of methyl isothiocyanate is 119° C.); the vapour pressure at 25° C. of allyl isothiocyanate is 5 mmHg, against 19 mmHg of methyl isothiocyanate, and it has a specific germination-preventing action.

In particular, it has been found that allyl isothiocyanate has a germination-preventing activity, but, due to its chemical characteristics and extremely low dosages for the use, it cannot be used as such. It must therefore be formulated in specific compositions which are easy to store for reasonably long periods of time, safe for workers, having a homogeneous distribution, with a well-defined efficacy time, a selective action on non-germinated seeds, no negative side-effects on the germinated seeds, with the possibility of being used in closed areas such as greenhouses.

SUMMARY OF THE INVENTION

An object of the present invention therefore relates to the preparation of compositions or formulates to be used in agriculture as germination-preventing products, comprising, as active principle, the compound allyl isothiocyanate, alone or combined with other substances having a synergic action.

According to a first embodiment of the invention, the formulate is a micro-encapsulated product comprising ITA, englobed in a polymeric-based system, for the controlled release of the active principle. The micro-encapsulated formulate is obtained through a micro-encapsulation process carried out by interfacial emulsion polymerization of the oil-in-water (O/W) type.

According to another embodiment of the invention, the formulate is an emulsion comprising ITA in the form of spherical liquid particles as emulsifiable formulates. The formulate is obtained through a water-oil emulsion process easy to effect even in fields.

Another object of the invention relates to the use of said formulations in agriculture for the selective disinfestation of fields under pre and post-emergence conditions.

A further object relates to the preparation of a process for the treatment of soil in agriculture, said process being based on the use of ITA and, in particular, the use of compositions having a germination-preventing activity comprising ITA as active principle, possibly in a synergic combination with other substances, in particular in the form of emulsions and micro-encapsulated formulations.

Further objects will be evident from the following detailed description of the invention.

DETAILED DESCRIPTION OF THE INVENTION

The terms "formulation" and "composition" will be used hereafter with the same meaning and will therefore be considered as being a synonym; the term "active principle" indicates the compound or mixture of compounds comprising allyl isothiocyanate having a germination-preventing action.

The active principle having a germination-preventing action, according to the present invention, is allyl isothiocyanate which, even in minimum amounts of 4 g per square meter of soil, has a marked germination-preventing action. The negative aspects of this product have already been mentioned, its use is therefore subordinate to the possibility of formulating it in compositions so that it can be safely handled, easily stored in liquid or solid form and, above all, the formulation should allow a homogeneous distribution of the active principle in the soil.

In accordance with the present invention, it is possible to proceed, after a few hours, with the bedding of seedlings already formed in soil treated with formulates containing allyl isothiocyanate. Again according to the present patent, in the case of direct sowing a deficiency period of at least 7-14 days must be respected.

Furthermore, the formulation must allow the active principle to remain in the soil for not more than 20 days, preferably 15 days or even less, and the treatment should possibly be able to be safely repeated, mainly in confined areas, such as greenhouses.

Normally, the quantity of ITA as active principle required in the treatment of soil can be lower than 5 g/m$^2$.

In a typical embodiment, 4 g/m$^2$ of ITA is used. An adequate formulation with respect to the treatment envisaged is requested due to the small quantities and consequent necessity of uniformly distributing the specific active principle with respect to the soil.

The germination-preventing action of ITA is also improved by the presence in the formulation of specific co-formulating compounds such as chloropicrin, 1,3-dichloropropene, eugenol, 1,8-cineole, isoborneole, isoprene.

According to a first preferred embodiment of the invention, the formulations are prepared by the microencapsulation of the active principle to control the release rate of the same. Microencapsulation is obtained by interfacial polymerization of the oil-in-water (O/W) type, and the production of a membrane of the polyurea/polyurethane type to delay the release of the active principles. The microencapsulation technique via interfacial polymerization, is well known. In the monograph "Microencapsulation—Methods and industrial applications" Simon Benita—Ed.: Marcel Dekker, 1996, New York, ISBN 0824797035, for example, the scientific bases and technological considerations are provided on which the microencapsulation technique by interfacial polymerization is based.

In accordance with the present invention, a solution of the active principle, in the compositions described below, are confined inside the microcapsules. Said preparations have a marked germination-preventing activity and can be used as active systems in agricultural activities. These preparations can be administered by using the procedures and techniques known to experts in the field and already used in the fumigation of soil with methyl bromide and chloropicrin.

Microcapsules are prepared by means of interfacial emulsion polymerization of the "oil-in-water" (O/W) type, through suitable monomers, such as, for example, polyisocyanates and polyamines, polyureas and/or polyalcohols (see MICROENCAPSULATION).

The microcapsules can be obtained by following a procedure with the following reaction steps:
  preparation of the organic phase consisting of one of the monomers or mixtures thereof described according to the present patent and containing isocyanate units. The active principle, containing ITA, is mixed with the monomer. A suitable solvent can be added to the organic phase, as dispersing agent of the active principle and fluidity and viscosity regulator of the same phase. The organic phase is in a liquid aggregation state;
  preparation of the aqueous phase by dissolving a suitable surfactant or blends of surfactants in water, according to what is described in the present patent;
  the aqueous phase is added to the organic phase and the whole mixture is stirred in order to obtain a stable emulsion;
  the second monomer or blend of hydrosoluble monomers (polyalcohols, polyureas, and/or polyamides) is added to the emulsion, kept under constant stirring, reactive with the present isocyanate in the organic phase, selected in accordance with the present patent;
  the reaction is normally carried out at room temperature, with a maximum temperature of 60° C. The microcapsules formed can be separated by filtration on sieves or stored and subsequently used as aqueous suspension as such.

Various substances, having a synergic action on the germination-preventing activity, such as chloropicrin, 1,3-dichloropropene, eugenol, 1,8-cineol, citral, isoborneol, isoprene, can be inserted in the microencapsulated formulate. The mixture of said active principles and co-formulating agents is generally always in a liquid aggregation state. In particular, chloropicrin and 1,3-dichloropropene become part of the liquid mixture confined inside the microcapsules in a blend with the other active components in order to increase the biocide properties.

In the preparations described in the present invention, the monomers used in the interfacial polymerization, soluble in the organic phase, are diisocyanates and polyisocyanates and blends thereof, preferably selected from the following compounds: poly[(phenyl isocyanate)-co-formaldehyde] having an average molecular weight within the range of about 300-400, 4,4',4''-triphenyl methane triisocyanate, biphenyl methane diisocyanate, hexamethylene diisocyanate, trimethylene diisocyanate, tetramethylene diisocyanate, 1,2-propylene diisocyanate, 1,2-butylene diisocyanate, 2,6-toluene diisocyanate, 1,4-cyclohexane diisocyanate. The composition of the mixtures of monomers which, in addition, controls the crosslinking degree, is established on the basis of the properties and membrane morphology to be obtained. In order to enhance the crosslinking degree, the mixture is enriched with the polyisocyanates component containing three or more reactive isocyanate groups. To prepare less resistant membranes, and therefore less crosslinked, the mixture is enriched with diisocyanate having only two isocyanate groups available for each molecule of monomer.

The organic phase in which the above monomers are dissolved normally consists of the same active principle. In order to make the mixture compatible for forming a stable solution, organic solvents such as the esters of acetic acid: ethyl acetate, propyl acetate, butyl acetate, pentyl acetate, are possibly used.

In the formulations according to the present invention, the monomers used in the interfacial polymerization, soluble in the aqueous phase, belong to the group of amines and alcohols. As far as the amines are concerned, the preferred formulation, according to the present patent, contain for example: diamines, polyamines, polyallyl amines, urea and its derivatives, melamine, hydrazine, ethylene diamine, propylene diamine, butylene diamine, pentamethylene diamine, hexamethylene diamine, diethylene triamine, triethylene tetramine, and all possible combinations of said monomers on the basis of the crosslinking degree which is expected in the polymerization. Branched bifunctional and/or polyfunctional monomers can be used in order to modulate the membrane property of the microcapsules. As far as the alcohols are concerned, the preferred formulations, according to this patent, contain: ethylene glycol, diethylene glycol, propylene glycol, 1,4-butandiole, 1,8-octane diole, 4,4'-dihydroxy-diphenyl methane, polyvinyl alcohol, polyethylene glycols, polypropylene glycols, polybutylene glycols at different molecular weights within the range of 200-3000.

The interfacial polymerization is carried out in emulsion, also with the help of a suitable surfactant, added in such a quantity as to control the dimensions of the microcapsules according to requirements. The preferred dimension range is 10-500 microns. Some emulsifying agents, of the ionic or non-ionic type, can be used for the purpose. Among the emulsifying agents of the ionic type, sodium stearate is used, as well as sodium dodecylsulphate, sodium dodecylbenzene-sulphonate, hexadecyltrimethylammonium bromide, alkyl aryl sulphonate. Among emulsifiers of the non-ionic type, polysorbate Tween 20 is used, as well as polysorbate Tween 40, polysorbate Tween 60, polysorbate Tween 80, Span 60, Span 80 and sodium alkylpolyglycol sulphates. In addition to the common ionic and non-ionic additives, partially hydrophilic polymers are also used, such as: polyallylamines, polyvinyl alcohol, carboxymethyl cellulose.

The polymerization can also be carried out in the presence of suitable catalysts in order to regulate the reaction rate and thus indirectly modulate the morphology of the microcapsule membrane. The addition of zinc chloride, for example, allows the polymerization to be accelerated and consequently to effect the microencapsulation, for particular formulates, at lower temperatures when the mixture of active principles and coformulants are too volatile.

The interfacial polymerization is carried out within a temperature range of 10-30° C., but the thermal treatment is pushed up to 60° C. according to the membrane morphology which is to be induced in the microcapsules and the type of monomers used. In particular, the high temperature treatment tends to reinforce the microcapsule walls, slowing down the release of the active principles and coformulants.

The microcapsule formulate, according to the present invention, is characterized by an extremely variable composition. The membrane normally represents a weight percentage of the microcapsules contained within the range of 5-25%, the surfactant forms a weight percentage of the microcapsules contained within the range of 2-10%, the quantity of active principle containing ITA represents a weight percentage of the microcapsules not lower than 70%.

Allyl isothiocyanate, chloropicrin, 1,3-dichloropropene are included as active principles and coformulants in a preferred microencapsulated preparation, according to the present invention. In the relative ratios, the allyl isothiocyanate is present, as active principle, in a ratio not lower than 2% by weight with respect to the coformulants, in some preferred coformulants however, it can be used 100% pure.

The microencapsulated nature of the formulation allows the solution to be slowly released into the soil, exerting a germination-preventing action over a prolonged period of time depending on the specific treatment requirements. The duration of the release depends on the chemical nature, the thickness and morphology of the membrane of the microcapsules. With his knowledge and disclosures obtained from "MICROENCAPSULATION", together with those of the present description, an expert in the field is capable of producing microcapsules consonant to the purposes of the present invention.

The microencapsulated formulate is particularly advantageous as it considerably reduces exposure of the operators to the fumes of the active principles and their coformulants. The covering membrane of the microcapsules acts as an actual container of the germination-preventing solution, thus reducing the undesired release of the active principles and coformulants into the operating environment. The microencapsulated formulate is therefore particularly suitable for both guaranteeing safety conditions in storage and for administration in closed environments as in the case of greenhouses.

According to another preferred embodiment of the invention, the preparation of emulsifiable formulates of active principle containing ITA is described. The preparation of emulsions with the use of surfactants is well known and is described in numerous scientific publications and monographs (see for example: "Emulsions and Emulsion Technology Part 1 (Surfactant Science)" published by Kenneth J. Lissant, Marcel Dekker publisher, ISBN: 0824760972, "Encyclopedia of Emulsion Technology: Applications" published by Paul Becher and Schuster Schuster, Marcel Dekker publisher, ISBN: 0824718771; "Encyclopedic Handbook of Emuslion Technology", published by Johan Sjoblom, CRC publisher, ISBN: 0824704541). The emulsifiable formulates are used for the preparation of emulsions by simple dispersion in water, added in suitable quantities.

Various emulsifying agents of both the ionic and non-ionic type are components of the emulsifiable formulations. Among emulsifying agents of the ionic type, sodium stearate, sodium dodecyl sulphate, sodium dodecylbenzenesulphonate, hexadecyltrimethylammonium bromide, alkylarylsulphonates, are used. Among emulsifying agents of the non-ionic type, polysorbate Tween 20, polysorbate Tween 40, polysorbate Tween 60, polysorbate Tween 80, Span 60, Span 80 and sodium alkylpolyglycol sulphates, can be used.

The active principle containing ITA is of a hydrophobic nature and consequently the emulsifying agent has the function of favouring its dispersion in water during the dilution in order to obtain a system with as uniform a composition as possible to favour a repeatable administration to the soil.

The emulsifiable formulation allows the penetration of the active principle to be increased in the soil as it is itself added to the formulate in the liquid state and therefore at a very high active concentration compared with the analogous concentration obtained by evaporation, as in some of the normal fumigation techniques. Furthermore, the uniform dispersion of the active principle guaranteed by the emulsifiable preparation ensures a homogeneous distribution in the soil, with a more repeatable action and thus guaranteeing the definition of a clear and reliable applicative procedure.

The administration of emulsifiable formulates with a germination-preventing action according to the present invention is effected in accordance with fumigation methods based on methyl bromide. The possibility of preparing the emulsions directly on the administration site with the use of on-line emulsion systems makes the formulation extremely versatile and optimum in terms of costs and feasibility. It is not necessary, for example, to store the formulate or to transport huge quantities of material, as the water necessary for the formation of an emulsion can be added directly on site.

According to an objective of the present invention, the emulsifiable formulate has a content of active principle containing ITA within the range of 70%-98% by weight, whereas the agent or mixture of surfactants is within an approximate range of 2-30% by weight.

Chloropicrin and 1,3-dichloropropene can be cited as coformulants, according to a preferred preparation, in a percentage quantity within the range of 50-96% by weight. In the relative ratios, the allyl isothiocyanate is present, as active principle, in a ratio not lower than 2% by weight with respect to the coformulants, but in some preferred formulates it can be used 100% pure.

Once the emulsifiable formulate has been dispersed in water according to the present invention, it reduces exposure of the administration operators to fumes of the active principle. The separation membrane between the internal oily phase and the outer aqueous phase confines the active principle containing ITA, thus diminishing undesired release into the operating environment. This formulate is therefore particularly suitable where operating conditions imply a very high risk of exposure for the operators. The formulate in emulsion-form is consequently extremely promising in the case of applications in closed environments as in the case of greenhouse crops.

A further object of the invention relates to the preparation of a process for the treatment of soil in agriculture, said process being based on the use of compositions with a germination-preventing activity containing ITA and coformulants according to the present patent.

The administration techniques firstly depend on the type of formulate adopted and type of treatment envisaged for the soil. Two types of techniques are normally adopted for fumigation:

administration by direct injection: in this case, the compound to be added to the soil, in the form of gas or liquid suspension, is injected with suitable needles to a depth which considerably depends on the type of crop, the action depth to be guaranteed and the type of product to be administered. If the formulate is in the gaseous state, a greater injection depth must be envisaged to avoid a sudden and undesired dispersion of the preparation, with a loss in the efficacy of the treatment. Due to its very nature, the administration method by direct injection is particularly useful in open fields, where automatic applications can be easily effected with suitable machinery for the purpose. Administration by direct injection is also applied in confined environments such as greenhouses, even if in this case machines must be used which are capable of operating in more restricted environments with numerous obstacles;

fertirrigation administration: in this case, the formulate is diluted in water and dispersed in the soil by means of irrigation ducts. The advantage lies in the greater simplicity and economical aspect of the process. One of the drawbacks lies in the poor control of the penetration depth of the formulate in the soil and a non-homogenous surface distribution. Furthermore, as it is distributed on the surface, if the active principle is particularly volatile, it is dispersed in the environment. Due to its very nature, the fertirrigation administration method is reserved, for particularly volatile active principles, to confined environments as in the case of greenhouses, where the dispersion is in any case reduced with respect to open fields.

The preferred administration procedure, according to the formulate considered in accordance with the present invention, can be schematized as follows:

administration by direct injection: both of the formulates claimed, microencapsulated and emulsifiable, can be easily distributed with this procedure. In the preferred procedure, the addition by injection of the formulates in the form of microcapsules is only recommended for confined environments such as greenhouses. For use in open fields, on the basis of a simple economical consideration, the use of emulsifiable formulates is more convenient. The emulsifiable formulations can therefore be distributed, after adequate dispersion in water, by direct injection both in confined environments (in greenhouses) and in open fields.

fertirrigation administration: this procedure can only be used for emulsifiable preparations, as the spontaneous penetration of microcapsules into the soil once they have been dispersed with water on the surface of the soil, is not always effective.

In a preferred administration by direct injection into the soil of a germination-preventing formulate according to the present invention, the following time process is adopted:

in pre-emergence: for the microencapsulated formulate and emulsifiable formulate, direct injection is effected to a depth of about 15-20 cm, i.e. only in the layer of active soil relating to the root system. In the case of emulsifiable formulates, administration can also be effected by fertirrigation, after direct dispersion in water. After the treatment a certain deficiency time of about 7-14 days must be respected, in accordance with the present invention. After this period it is possible to proceed with the direct sowing.

in post-emergence: for the microencapsulated formulate and emulsifiable formulate, direct injection is effected to a depth of about 15-20 cm, i.e. only in the layer of active soil relating to the root system. In the case of emulsifiable formulates, administration can also be effected by fertirrigation, after direct dispersion in water. After administration, it is preferable to wait a few hours before proceeding with the embedding of seedlings already cultivated.

The following examples are provided for illustrative and non-limiting purposes of the scope of the present invention.
Materials and Methods All the reagents and chemical solvents were purchased from Aldrich and Fluka, and used without any further purification. The emulsions were prepared using a Silverson L4RT mixer-emulsifier (Silverson Machines, Inc., East Longmeadow, Mass.). The mechanical stirring was effected with the help of a rod mixer of VELP Scientifica stirrer model DLH. The thermogravimetric analyses (TGA) were carried out with the help of a thermogravimetric analyser of TA Instruments, model Q500 with a heating rate of 20° C./min. The samples were analyzed within a temperature range of 30-550° C., under a stream of nitrogen. The FT-IR spectroscopic analysis was effected by incorporating the samples in the form of KBr tablets and analyzing them within a wave-number range of 4000-400 $cm^{-1}$ by means of a Nexus ThermoNicolet spectrometer. The synthesized microcapsules were analyzed to determine their dimension distribution by means of a Malvern Mod. Master-sizer S laser. For this purpose, samples of dried microcapsules were dispersed in distilled water containing 1% of Tween 20 as surfactant and sonicated in a sonication bath for 1 min. A Zeiss optical microscope model Axioskop 40 A Pol (Carl Zeiss, Germany), was used for the optical measurements. The electron scan microscopy was carried out with a LEO 420 electron microscope (LEO Electron Microscopy Ltd.). Before being subjected to analysis, the samples were placed on an aluminum support and covered with an AuPd alloy using a high vacuum sputter coated.

EXAMPLES OF FORMULATIONS

Example 1

Microencapsulated Formulation of Allyl Isothiocyanate

The aqueous phase is prepared by dissolving 0.50 g of TWEEN 80 in 100 ml of water. The organic phase is prepared by dissolving 3.0 g of poly[(phenylisocyanate)-co-formaldehyde] ($M_n$ about 400) and 10.0 g of allyl isothiocyanate in 3 ml of pentylacetate. The two phases are emulsified with the help of a Silverson mixer mod. 14RT at a rate of about 3000 r.p.m. for 3 minutes. The mixture is stirred with a rod mixer at 350 r.p.m. An aqueous solution is added, obtained by diluting 1.50 g of hydrazine in 30 ml of water. The system is left to react for about three hours. At the end, the aqueous suspension of microcapsules can be used as such or filtered on a glass filter and left to dry until an extremely fine powder is obtained, depending on the specific applications.

Figure 1:
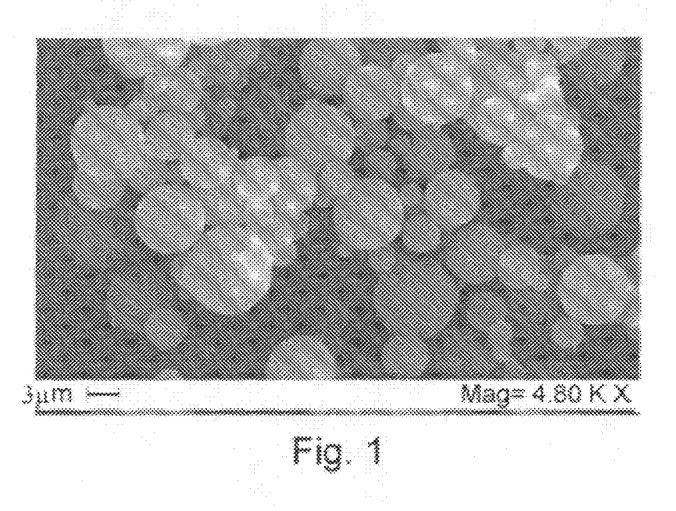
FIG. 1. Electron microscope image of a microcapsule sample (Example 1)
Figure 2:
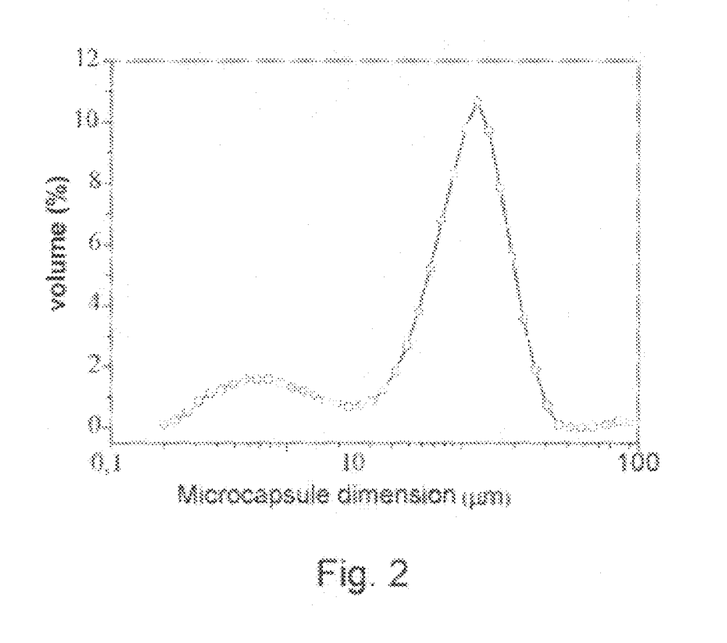
FIG. 2. Microcapsule dimension distribution (Example 1)
Figure 3:
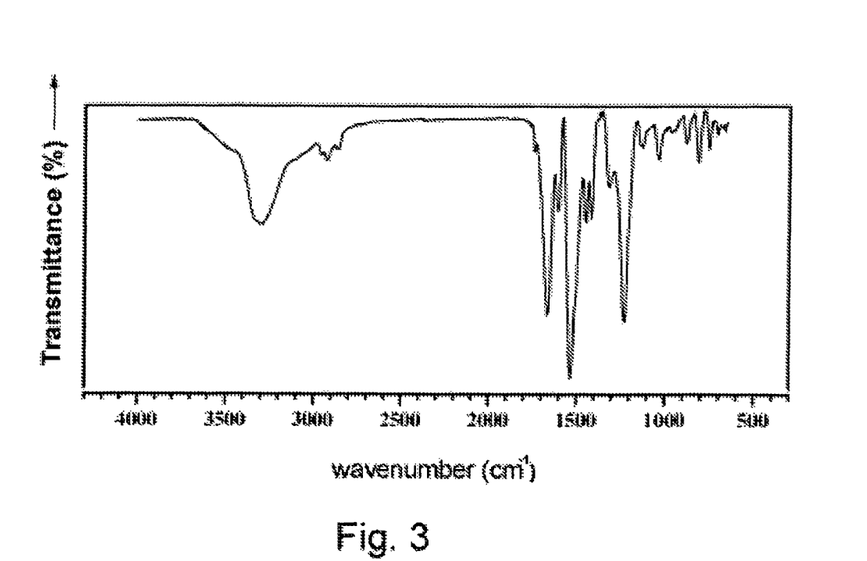
FIG. 3. FT-IR spectrum of a microcapsule sample (Example 1)
Figure 4:
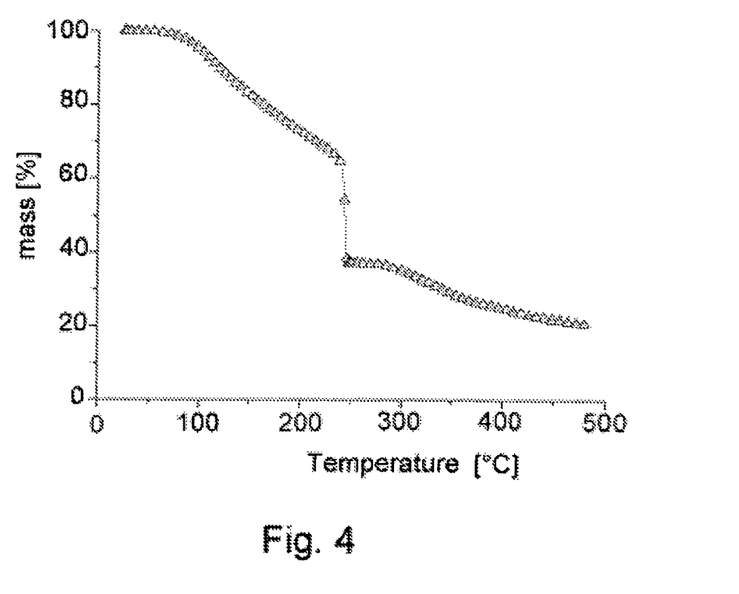
FIG. 4. TGA sample of microcapsules (Example 1)

FIGS. 1 and 2 respectively indicate the electronic microscopic image of the microcapsules and their dimension distribution curve. The microcapsules are free of residual isocyanate as shown in the infrared spectrum of a sample of microcapsules illustrated in FIG. 3. The weight loss is indicated by the thermogravimetric trace shown in FIG. 4, characterized by a sudden release of the contents of the microcapsules at about 250° C. The average dimension of the microcapsules is within the range of 10-20 μm.

Example 2

Microencapsulated Formulation of Allyl Isothiocyanate/chloropicrin 25%/75% by Weight The aqueous phase is prepared by dissolving 1.0 g of sodium dodecyl benzenesulphonate in 100 ml of water. The organic phase is prepared by dissolving 3.0 g of poly[(phenyl isocyanate)-co-formaldehyde] ($M_n$ about 400) in a mixture of 5 g of allyl isothiocyanate and 15 g of chloropicrin. The two phases are emulsified with a rod mixer at a rate of about 350 r.p.m. for 3 minutes at room temperature. During the emulsification an aqueous solution is added, obtained by diluting 0.70 g of ethylenediamine in 30 ml of water. The reaction is carried out for about three hours. At the end of the reaction, the preparation is preserved as such ready for use.

Figure 5:
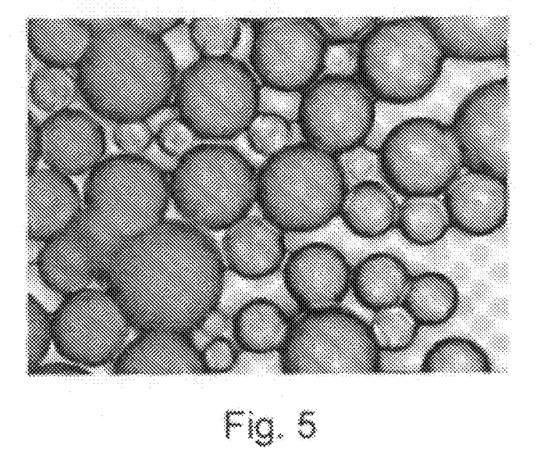
FIG. 5. Optical microscope image of a sample of a microcapsule (Example 2) suspended in water FIG. 6. TGA of a microcapsule sample (Example 2) after filtration and drying at room temperature FIG. 7. Optical microscope image of a germination-preventing emulsion containing allyl isothiocyanate (Example 3)
Figure 6:
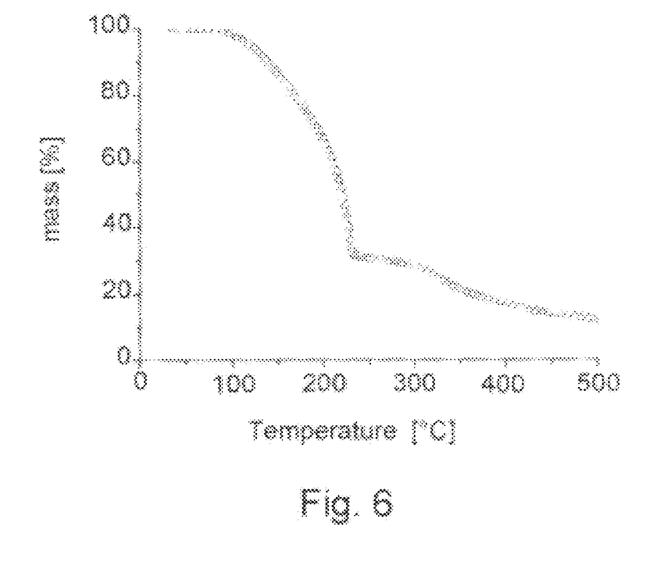

FIGS. 5 and 6 respectively indicate the optical microscopic image of the microcapsules and the thermogravimetric trace, characterized by a continuous release of the contents of the microcapsules starting from about 100° C. The dimension of the microcapsules is within the range of 100-400 μm.

Example 3

Emulsifiable Formulation of Allyl Isothiocyanate

A quantity of 400 g of allyl isothiocyanate is added to 0.800 liters of water containing about 10 g of ionic surfactant (alkylarylsulphonate). The system is emulsified and kept at 300 r.p.m. for 10 minutes.

Figure 7:
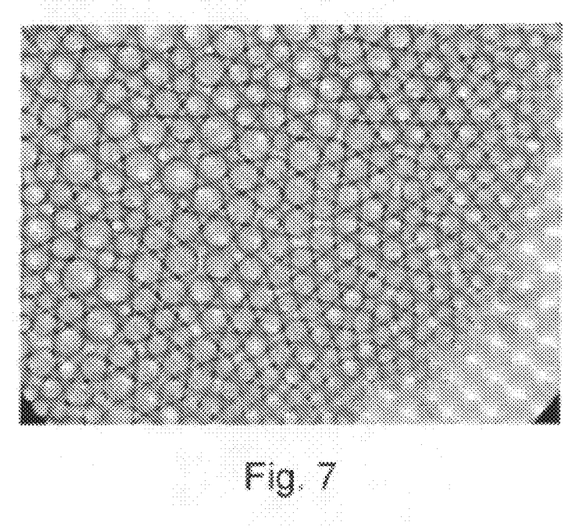

FIG. 7 shows the image of the formulate registered with a light transmission optical microscope. The dimension of the microcapsules is within the range of 50-100 μm.

The formulate thus obtained is dispersed in water before administration to the soil.

Example 4

Emulsifiable Formulation of Allyl Isothiocyanate/chloropicrin 20%/80% by Weight 40 g of allyl isothiocyanate and 160 g of chloropicrin are added to 0.400 liters of water containing 4 g of ionic surfactant (alkylarylsulphonate). The system is emulsified with a mechanical rod stirrer and kept at 300 r.p.m. for 10 minutes.

Figure 8:
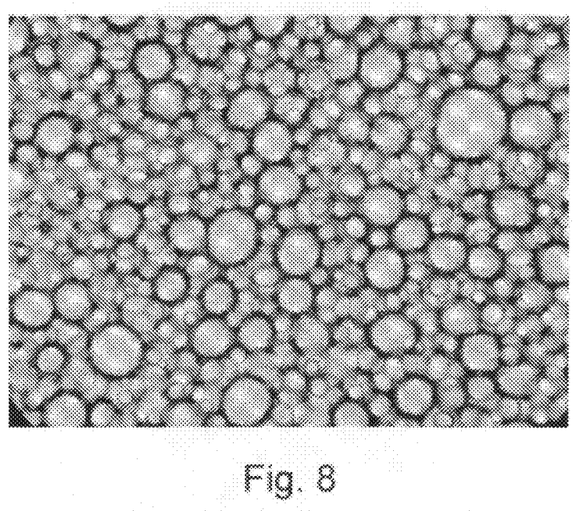
FIG. 8. Optical microscope image of a germination-preventing emulsion containing allyl isothiocyanate/chloropicrin (relative percentage 20%/80% by weight) (Example 4)

FIG. 8 shows the image of the formulate registered with a light transmission optical microscope. The dimension of the microcapsules is within the range of 50-100 μm.

The formulate thus obtained is dispersed in water before administration to the soil.

Example 5

Emulsifiable Formulation of Allyl Isothiocyanate/1,3-dichloropropene 30%/70% by Weight 60 g of allyl isothiocyanate and 140 g of dichloropropene are added to 0.400 liters of water containing 4 g of ionic surfactant (alkylarylsulphonate). The system is emulsified with a mechanical rod stirrer and kept at 300 r.p.m. for 10 minutes.

Figure 9:
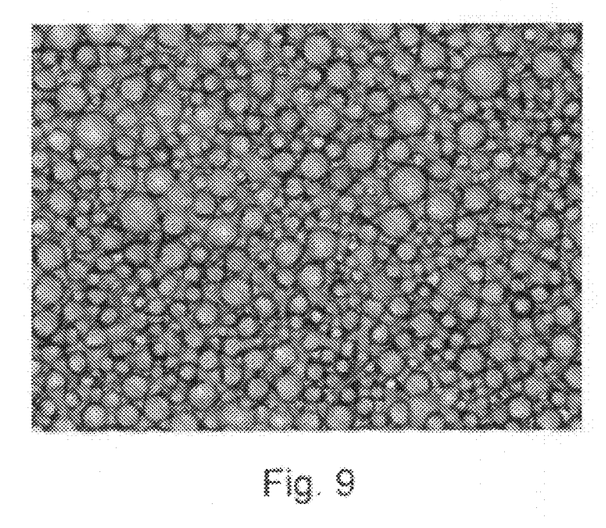
FIG. 9. Optical microscope image of a germination-preventing emulsion containing allyl isothiocyanate/1,3-dichloropropene (relative percentage 30%/70% by weight) (Example 5).

FIG. 9 shows the image of the formulate registered with a light transmission optical microscope. The dimension of the microcapsules is within the range of 50-100 μm.

The formulate thus obtained is dispersed in water before administration to the soil.

The invention claimed is:

1. A composition with a germination-preventing action in the form of an emulsifiable formulate consisting of allyl isothiocyanate, as an active ingredient and a non-ionic emulsifying agent selected from the group consisting of polyoxyethylene 20 sorbitan monolaurate, polyoxyethylene 20 sorbitan monopalmitate, polyoxyethylene 20 sorbitan monooleate, polyoxyethylene 20 sorbitan monostearate, sorbitan monostearate and sorbitan monooleate wherein said emulsifyable formulate has a content of said allyl isothiocyanate of 70-98% by weight and a content of said non-ionic emulsifying agent of 2-30% by weight.

2. An emulsion consisting of the emulsifiable formulate according to claim 1 dispersed in water.

3. A method for the treatment of soil in agriculture, comprising injecting the composition according to claim 1 into the soil to be treated.

4. A method for the treatment of soil in agriculture, comprising diluting the composition according to claim 1 in water and then administering to the soil by fertirrigation.

5. The method according to claim 3, wherein said method is applied in pre-emergence.

6. The method according to claim 3, wherein said method is applied in post-emergence.

7. The method according to claim 3, wherein allyl isothiocyanate is injected in a quantity not lower than 5 $g/m^2$.

8. The method according to claim 3, wherein allyl isothiocyanate is injected in a quantity equal to 4 $g/m^2$.

9. A composition with a germination-preventing action consisting of allyl isothiocyanate, as an active ingredient and chloropicrin as a coformulant, where 50-96% by weight of chloropicrin is present.

10. A composition with germination-preventing action consisting of allyl isothiocyanate, as an active ingredient and a synergic amount of chloropicrin as a coformulant.

* * * * *